(12) United States Patent
Mao et al.

(10) Patent No.: US 11,302,006 B2
(45) Date of Patent: *Apr. 12, 2022

(54) 3D QUANTITATIVE ANALYSIS WITH DEEP LEARNING

(71) Applicant: Topcon Corporation, Tokyo (JP)

(72) Inventors: Zaixing Mao, Tokyo (JP); Zhenguo Wang, Ridgewood, NJ (US); Kinpui Chan, Ridgewood, NJ (US); Yasufumi Fukuma, Tokyo (JP)

(73) Assignee: Topcon Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/103,058

(22) Filed: Nov. 24, 2020

(65) Prior Publication Data

US 2021/0082116 A1 Mar. 18, 2021

Related U.S. Application Data

(63) Continuation-in-part of application No. 16/277,319, filed on Feb. 15, 2019, now Pat. No. 10,878,574.

(60) Provisional application No. 62/633,363, filed on Feb. 21, 2018.

(51) Int. Cl.
*G06T 7/00* (2017.01)
*G06N 20/00* (2019.01)
*G06N 7/00* (2006.01)

(52) U.S. Cl.
CPC ........... *G06T 7/0014* (2013.01); *G06N 7/005* (2013.01); *G06N 20/00* (2019.01); *G06T 2207/10101* (2013.01); *G06T 2207/20076* (2013.01); *G06T 2207/20081* (2013.01); *G06T 2207/30041* (2013.01)

(58) Field of Classification Search
CPC ......... G06T 7/0014; G06T 2207/10101; G06T 2207/20076; G06T 2207/20081; G06T 2207/30041; G06N 20/00; G06N 7/005
USPC ........................................................ 382/128
See application file for complete search history.

(56) References Cited

U.S. PATENT DOCUMENTS

| 2011/0182517 | A1 | 7/2011 | Farsiu et al. |
| 2017/0119242 | A1* | 5/2017 | Jia ............................. G06T 7/11 |
| 2017/0164825 | A1* | 6/2017 | Chen ...................... G01N 21/47 |
| 2017/0287137 | A1 | 10/2017 | Lin et al. |

(Continued)

FOREIGN PATENT DOCUMENTS

CN 103514605 A 1/2014

OTHER PUBLICATIONS

Alonso-Caneiro, David, et al., Automatic segmentation of choroidal thickness in optical coherence tomography. Biomedical Optics Express, vol. 4, Issue 12, Nov. 11, 2013, pp. 2795-2812.

(Continued)

*Primary Examiner* — Wednel Cadeau
(74) *Attorney, Agent, or Firm* — Pearne & Gordon LLP

(57) ABSTRACT

A machine learning model is trained to identify the texture difference between the different layers of a multilayer object. By training with data in full 3D space, the resulting model is capable of predicting the probability that each pixel in a 3D image belongs to a certain layer. With the resulting probability map, comparing probabilities allows one to determine boundaries between layers, and/or other properties and useful information such as volume data.

19 Claims, 12 Drawing Sheets

(56) References Cited

U.S. PATENT DOCUMENTS

2018/0012359 A1    1/2018  Prentasic et al.

OTHER PUBLICATIONS

Zhang, Li, et al., "Automated Segmentation of the Choroid from Clinical SD-OCT", Investigative Ophthalmology & Visual Science, vol. 53, No. 12, Nov. 2012, pp. 7510-7519.

Xiaodan Sui, Yuanjie Zheng, Benzhen Wei, Hongsheng Bi, Jianfeng Wu, Xuemei Pan, Yilong Yin and Shaoting Zhang, Choroid segmentation from optical coherence tomography with graph-edge weights learned from deep convolutional neural networks. Neurocomputing 237 (2017), pp. 332-341.

Yang, Q., Reisman, C.A., Wang, Z., Fukuma, Y., Hangai, M., Yoshimura, N., Tomidokoro, A., Araie, M., Raza, A.S., Hood, D.C. and Chan, K., 2010. Automated layer segmentation of macular OCT images using dual-scale gradient information. Optics express, vol. 18, No. 20, Sep. 27, 2010, pp. 21293-21307.

European Search and Written Opinion for European Application No. 19158556.1 dated Jul. 19, 2019.

Carson Lam et al., "Retinal Lesion Detection with Deep Learning Using Image Patches", Jan. 1, 2018 (Jan. 1, 2018), XP055594611, Retrieved from the Internet: URL:https://www.ncbi.nim.nih.gov/pmc/articles/PMC5788045/pdf/i1552-5783-59-1-590.pdf, pp. 590-596.

* cited by examiner

3D QUANTITATIVE ANALYSIS WITH DEEP LEARNING

CROSS REFERENCE TO RELATED APPLICATIONS

This application is a continuation-in-part of U.S. patent application Ser. No. 16/277,319, filed on Feb. 15, 2019, entitled "3D QUANTITATIVE ANALYSIS OF RETINAL LAYERS WITH DEEP LEARNING", which claims priority to U.S. Provisional Application Ser. No. 62/633,363, filed on Feb. 21, 2018, entitled "3D QUANTITATIVE ANALYSIS OF RETINAL LAYERS WITH DEEP LEARNING", the entireties of which are incorporated herein by reference.

BACKGROUND

The present disclosure relates to quantitative analysis of physiological images with deep learning algorithms and artificial intelligence. More particularly, the disclosure relates to identification and analysis of ophthalmic tissue in optical coherence tomography (OCT) images and volumes, and two-dimensional (2D) images and three-dimensional (3D) volumes from other imaging sources.

Current OCT systems (such as those using light sources in the 1 μm spectral range region) enable visualization of the different tissue layers in the retina. However, despite such advancements in OCT technology, quantitative analysis of the different layers is primarily based on segmentation techniques that rely on boundary detection within a cross sectional image (B-scan or B-frame).

For example, one common boundary detection method utilizes graph-search theory. But this can be particularly challenging between some layers such as the choroid and sclera, and between the ganglion cell layer (GCL) and the inner plexiform layer (IPL) due to the lack of well-defined physiological boundaries and/or the transparency of those layers. Other common methods suffer from similar deficiencies. Additionally, some approaches use a series of complex steps, such as building 3D models of the blood vessels to identify the choroid-sclera interface (CSI). The CSI is then constructed with a 'thin plate spline' (TPS) approach. But this assumes the CSI to be continuous and smooth, while biologically, there may be no clear physical boundary between the two layers.

BRIEF SUMMARY

According to a first example of the subject matter described herein, a method comprises training a machine learning system with at least two training images, a first of the training images being obtained from a first type of physiological tissue and a second of the training images being obtained from a second type of physiological tissue, the machine learning system being trained to recognize differences in the training images between the first and second types of physiological tissues; supplying the trained machine learning system with an image of a subject physiological tissue; with the trained machine learning system, identifying probabilities that pixels in the image belong to the first type of physiological tissue and/or the second type of physiological tissue, each probability corresponding to a pixel of the image; and based on the identified probabilities, identifying a boundary in the image between the first and second types of physiological tissues, or determining a property of the first or second type of physiological tissue.

According to various embodiments of the above example, the first type of physiological tissue and the second type of physiological tissue are different layers of a retina; the first type of physiological tissue is a choroid and the second type of physiological tissue is a sclera; the training images are 2D en face images; the 2D en face images are generated by flattening volumetric imaging data with respect to a reference layer; the reference layer is the Bruch's membrane; the 2D en face images are separated by a predetermined depth; the first training image is from a first 3D volume of training images and the second training image is from a second 3D volume of training images, a center of first 3D volume being a predetermined number of pixels from a center of the second 3D volume; the method further comprises generating a probability map for the pixels in the image supplied to the model, each pixel of the probability map representing the identified probability of a corresponding pixel of the image supplied to the model; the method further comprises comparing the identified probabilities for pixels in an A-line of the image to a predetermined threshold; a boundary pixel in the A-line is identified as the first pixel whose probability is equal to or greater than the predetermined threshold, the boundary pixel being a pixel of the identified boundary; a boundary pixel in the A-line is identified as the first pixel in a set of pixels, each pixel in the set of pixels having an identified probability that is equal to or greater than the predetermined threshold; the boundary in the image is identified according to a shortest path search technique; the boundary in the image is identified according to a machine learning technique; the method further comprises extracting each pixel in the image of the subject that is equal to or greater than a predetermine threshold; the extracted pixels form a 3D volume and the method further comprises displaying the 3D volume formed by the extracted pixels; the image is part of a 3D volume of images, a plurality of images of the 3D volume being supplied to the trained machine learning system and having a boundary between the first and second types of physiological tissues identified or a property of the first and second types of physiological tissues determined; the differences between the first and second training images are textural differences between the first and second types of physiological tissues; the method further comprises preprocessing the first or second training image prior to the machine learning system being trained; and/or the method further comprises preprocessing the image of the subject physiological tissue prior to supplying the trained machine learning system with the image.

DETAILED DESCRIPTION OF THE DRAWINGS

In view of the above-noted deficiencies, the present disclosure is based, in part, on the recognition that the texture appearance of different structural layers is different. Further, these differences can be analyzed and classified with machine learning based techniques with deep learning algorithms and artificial intelligence. The present disclosure thus relates to using machine learning for quantitative analysis in three dimensions. More particularly, the present disclosure relates to such analysis of optical coherence tomography (OCT) 3D imaging volume data for retinal structures/layers. However, it is to be understood that the method can be applied to images of any layers of a structure (e.g., any tissue layers of a physiological structure) taken by any imaging modality. For example, 3D imaging volume data may instead be obtained by a slit-lamp and the 3D data may be obtained as a series of cross-section images. The 3D data may also be of an anterior portion of the eye, such as a cornea.

Figure 1:
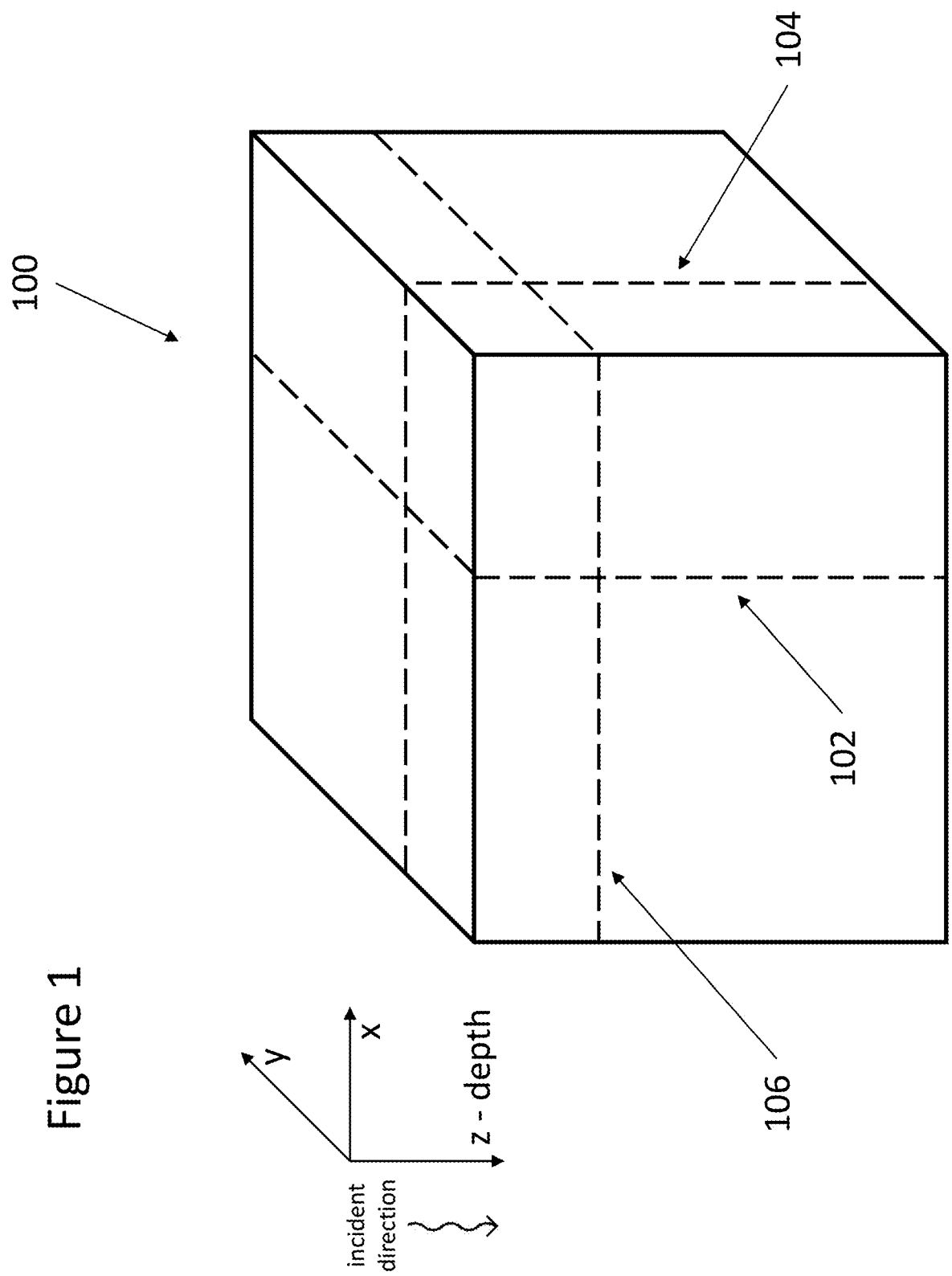
FIG. 1 illustrates example 3D volume data from an imaged object.

An example 3D volume data 100 is illustrated in FIG. 1. Using OCT as an example, and the 3D coordinate system in FIG. 1, incident light is shined in the z direction at each x-y location on an object being imaged to obtain the volume data 100. Relative to the 3D coordinate system then, the data obtained for incident light at each x-y location is referred to herein as an "A-line" or "A-scan"; a collection of A-lines in a y-z or x-z plane (forming a 2D image) is referred to herein as a "B-scan" or "B-frame" 102 (a y-z B-scan at a particular x location), 104 (an x-z B-scan at a particular y location); and a 2D image in the x-y plane at a particular z depth, or a projection in the x-y plane over a depth range (e.g., by averaging values, or performing some other statistical operation, across all depths in the range) is referred to herein as an "en face," "projection," or "flattened" image 106. When an en face image is formed over a depth range, that range may be defined with respect to an identified layer, for example, the Bruch's membrane (BM), choroid, or sclera.

Briefly, according to the present disclosure, a machine learning model is trained to identify the texture differences between the different layers of a multilayer object. By training with data in full 3D space, the resulting model is capable of predicting the probability that each pixel in a 3D image belongs to a certain layer. With the resulting probability map, useful information such as boundary and volume data can be extracted. In other words, the output of the machine learning system can be a probability that a particular pixel belongs to a particular layer. Comparing probabilities then allows one to determine the boundary between the layers, and/or other properties of the layers. A first example embodiment of this is illustrated in FIG. 2.

Figure 2:
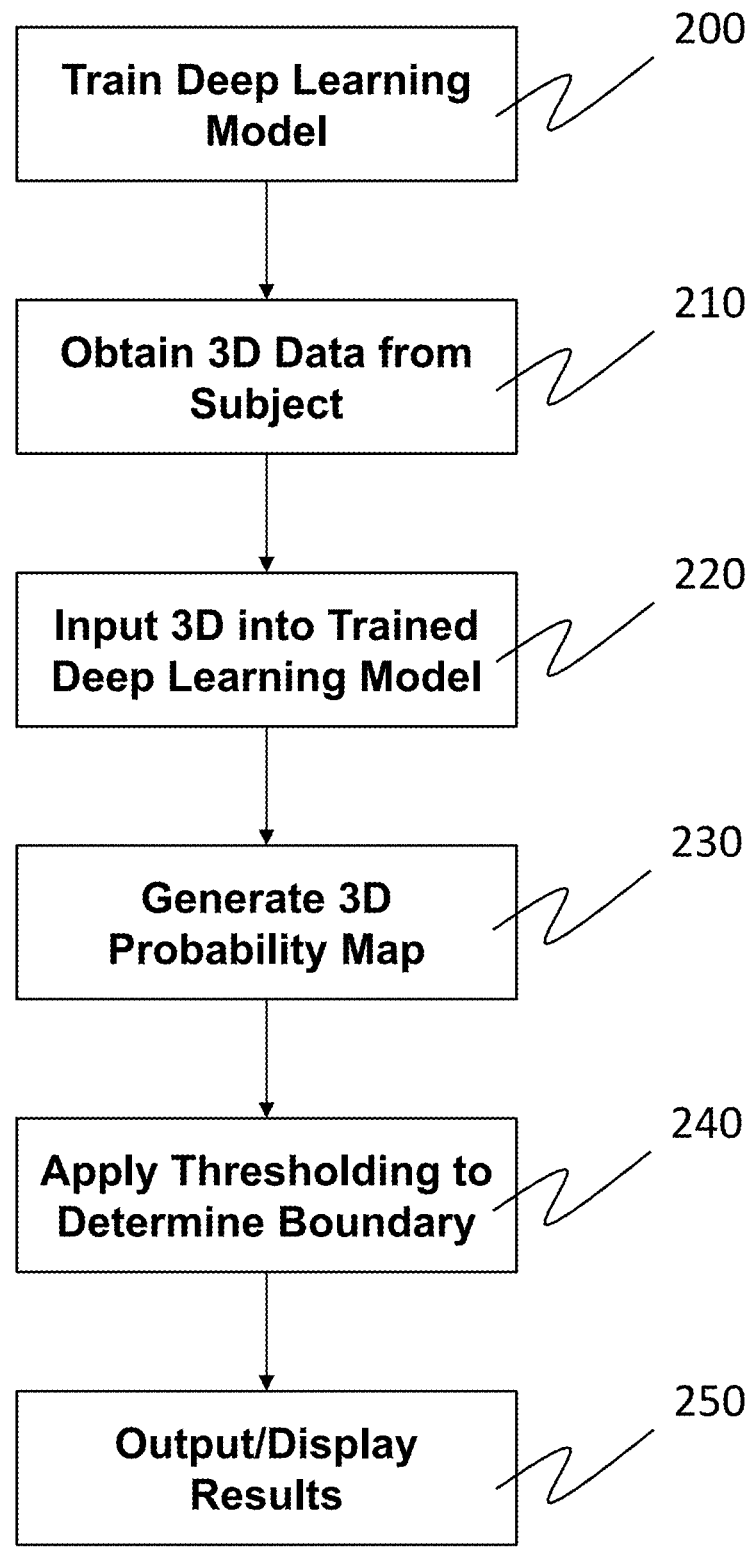
FIG. 2 illustrates a flow chart of a first example embodiment of the method described herein.

As shown in FIG. 2, a machine learning system (e.g., a deep learning model) used to perform the above described texture analysis is first trained 200 to differentiate between the textures of different layers (e.g., the choroid and sclera). This training is based on information extracted from 3D imaging volume data. Images used for training are taken from layers of interest (e.g., those on either side of a desired boundary identification) of a particular object (e.g., the human eye including the retina and/or cornea). These images can come from any data set, and do not necessarily need to be from a subject who the learned machine will ultimately analyze. Generally, since layers change most relative to depth, for training it is preferable to use en face 2D images (e.g., from an OCT volume or those from a 3D volume obtained by slit lamp), which as noted above, can be flattened with respect to a reference plane or layer (e.g., the Bruch's membrane). Of course, images from any modality and/or plane may be used, so long as the machine learning system is exposed to textures of the different layers of interest.

Figure 3:
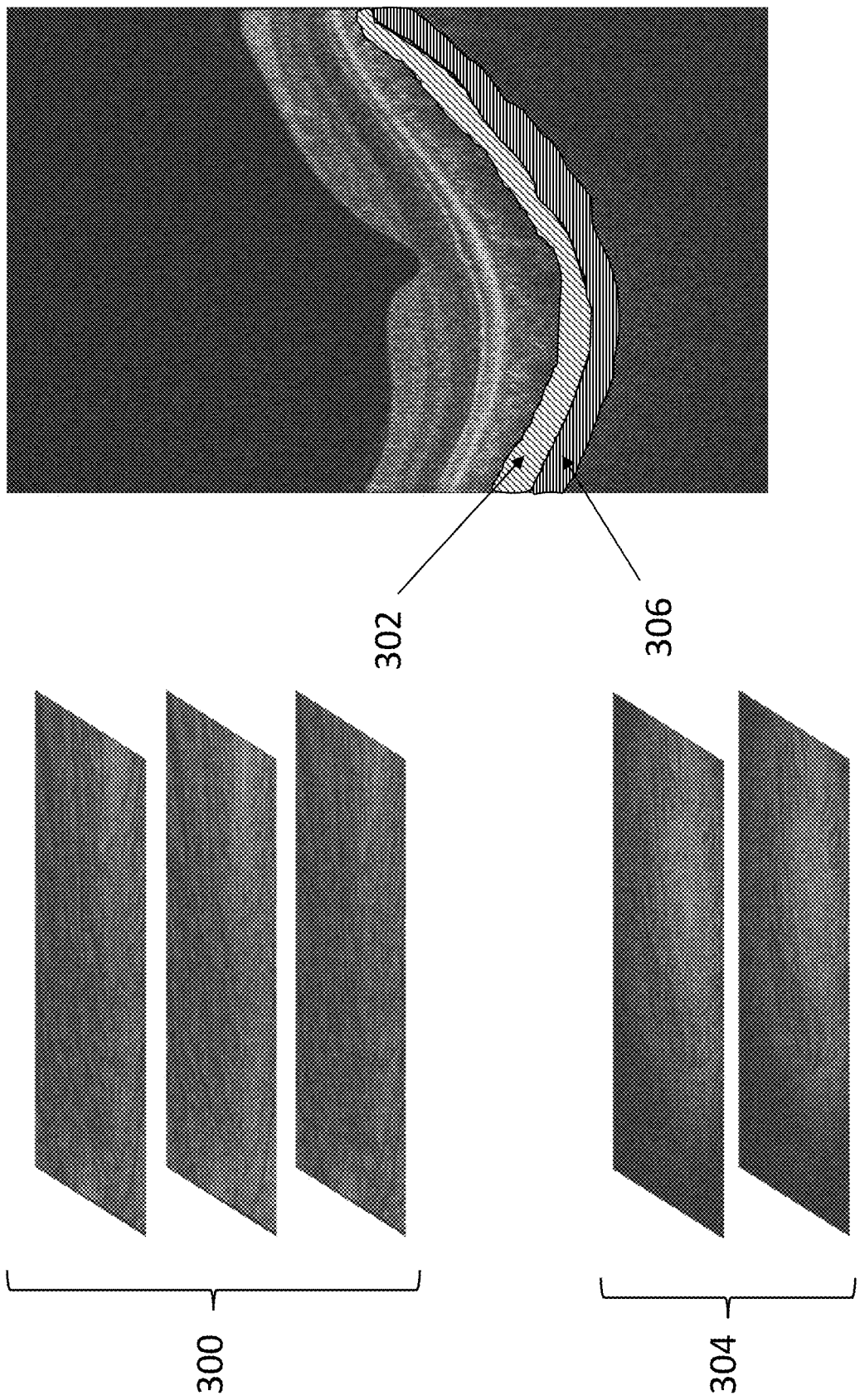
FIG. 3 illustrates example en face training images from different layers of the retina.

FIG. 3 illustrates example en face training images 300 representing the choroid 302 (shown in an associated B-scan of the retina), and images 304 of the sclera 306. During training, these images 300, 304 are input to the machine learning system with the known corresponding layer, so that the learned machine can associate the textures of the trained images with the corresponding layers. Training with images from the layers as shown in FIG. 3 would be used to train a machine learning system to identify whether pixels of images input thereto belong to the choroid or sclera, and subsequently identify a choroid-sclera boundary. In some embodiments, any or all of the training images 300, 304 may be may be preprocessed to reduce noise, improve contrast, or the like, prior to being input to the machine learning system.

Depending on the training embodiment, the training images may be input and processed for training by the machine learning system in many different forms. For example, as used herein, a "2D approach" refers to independently processing en face images representative of the layers. In other words, in the 2D approach, for each pixel of an en face training image, only the information in a single 2D en face image is used to train the machine learning system to determine a corresponding layer. Thus, the machine learning system correlates only that pixel to the corresponding layer.

Figure 4:
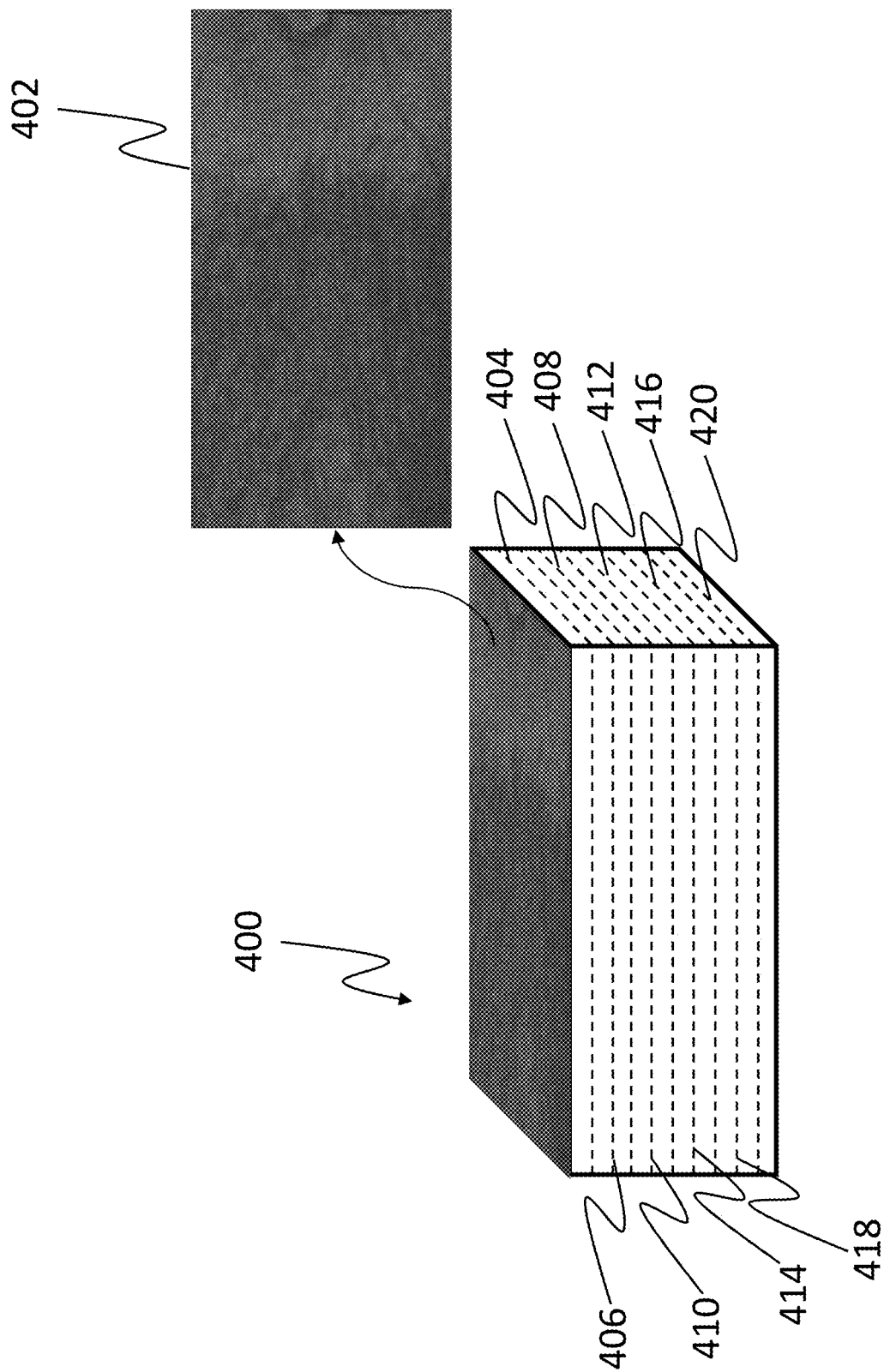
FIG. 4 illustrates a "2D sequential approach" to training a machine learning system.

FIG. 4 illustrates a "2D sequential approach" in which multiple en face images (forming a volume) are used to train the machine learning system to determine a layer designation of a pixel in a reference en face image. In the example of FIG. 4, a volume 400 having ten en face images (e.g., a 512×256×10 volume) is used to train the machine learning system, rather than single en face images individually as in the 2D approach. As illustrated, the ten en face images correspond to a depth of ten pixels, each pixel depth being represented by a different en face image 402-420. However, it is noted that the volume may be of any size, and the en face images may be the projection over a depth greater than one pixel. With the volume 400, the machine learning system first learns to determine a layer designation for the pixels of one of the ten en face images. The other nine images provide additional information for refinement. More particularly, the machine learning system looks at one en face image at a time, in a predetermined order from the images of the volume, to recognize variations in textures progressing through the volume. The additional information can come from en face images above and/or below a reference image of interest within the volume.

For example, considering an outermost image 402 of volume 400 as the reference, the machine learning system can learn to recognize the changes to pixels at corresponding X-Y location as one progresses inward through each additional image in the volume 400. Similarly, if the reference image is in the middle of the volume (e.g., at layer 412), the machine learning system can learn to recognize pixel variations above and/or below the reference image by looking to outward images in the volume and/or to downward images in the volume. In so doing, additional information along the z-axis (depth), such as the rate of texture change, is captured and processed during training of the machine learning system. This information can help improve the accuracy at predicting which layers pixels in an image belongs to.

Figure 5:
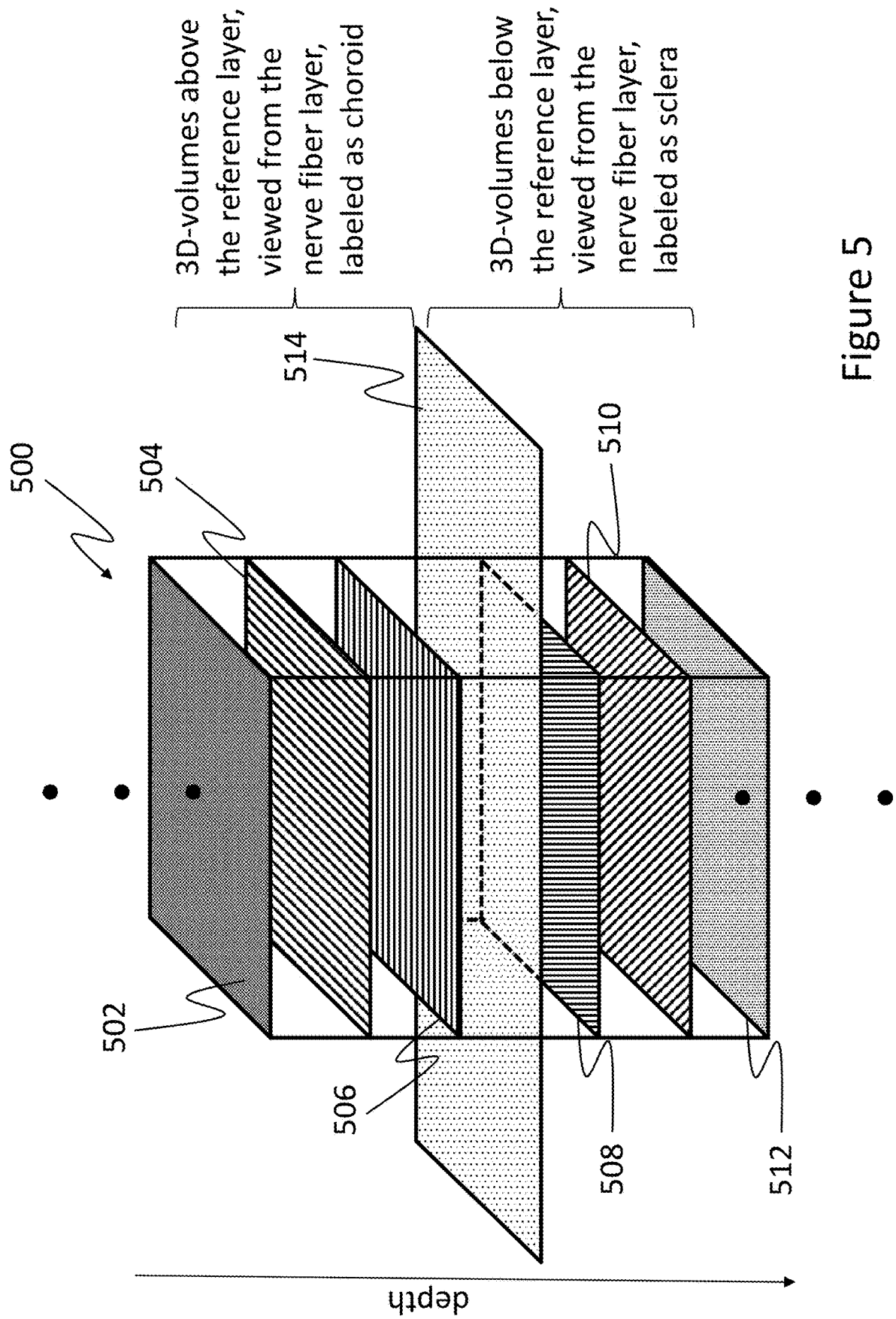
FIG. 5 illustrates a "3D approach" to training a machine learning system.

Another training embodiment described herein as a "3D approach" is illustrated in FIG. 5. The 3D approach is similar to the 2D sequential approach described above; however, rather than processing one 2D image of a volume at a time as in the 2D sequential approach, all 2D images of a 3D volume are considered at the same time, and multiple 3D volumes may be considered. With this, the machine learning system can learn to recognize texture variations within a plurality of 3D volumes taken from different depths of larger 3D volume data.

For example, FIG. 5 illustrates a portion of a large 3D volume 500 represented by a plurality of en face images 502-512 relative to a reference layer 514. The en face images may be images at a single depth or flattened over a depth range and thus representative of a sub-volume within volume 500. These en face images may be sequential, or separated by a particular, pre-determined depth (e.g., five pixels). In other embodiments, the 3D volume 500 may be represented directly by the sub-volumes, each sub-volume having a center depth separated by a particular, predetermined distance (e.g., five pixels). In this case, the layers 502-512 may be representative of en face images at the center depth of each of six sub-volumes. In any event, reference layer 514 may correspond to the boundary for which the machine learning system is being trained. Thus, using the above example of the CSI, the en face images or sub-volumes 502-506 above the reference layer 514 may be identified for training purposes as representative of the choroid; and en face images or sub-volumes 508-512 below the reference layer 514 may be identified for training purposes as representative of the sclera.

Each of the en face images or sub-volumes 502-512 (or combinations thereof) may be then processed together by the machine learning system for training, so that the system can learn to recognize variations throughout volume 500. Alternatively, each sub-volume may be processed individually for training, with each en face image comprising the sub-volumes processed together. While examples described and illustrated herein relate to particular numbers of en face images and sub-volumes, it is noted that any number may be used, and those images and sub-volumes may be separated by any distance.

Referring back to FIG. 2, 3D volume data is obtained 210 by imaging an object/subject (e.g., a subject's eye including the retina and/or cornea). While FIG. 2 illustrates that the 3D volume data is obtained after training the machine learning system, it is noted that the data may be obtained at any time. Once the machine learning system is trained (e.g., as a deep learning model), the obtained 3D volume data may be input 220 to the trained machine learning system. As with the training images, the obtained 3D volume data may be preprocessed to reduce noise, improve contrast, or the like, prior to being input to the machine learning system. Proceeding in a pixel-wise fashion, the machine learning system determines and outputs a probability that each pixel of the image data is part of a particular layer (e.g., the choroid or sclera). The machine learning system can then generate and/or output a volumetric probability map 230 of the layers of interest (as it is trained to do), which can later be used to identify boundaries. In other words, by looking at a plurality of en face or other 2D B-scan images from the input 3D volume data, the machine learning system can identify a probability that each pixel in the input 3D volume belongs to one of the layers the system is trained to recognize. These probabilistic values can be used to generate probability volume maps 230.

When inputting images into a learned machine learning model to perform the probability analysis, the images are preferably input in the same manner (according to the same approach) that was used to train the model. Thus, for the above-described training approaches, learned machines trained according to the "2D approach" take in 2D en face images (as explained above), while learned machines trained according to the "2D sequential approach" and "3D approach" would take in stacks of 2D en face images (volumes).

Figure 6:
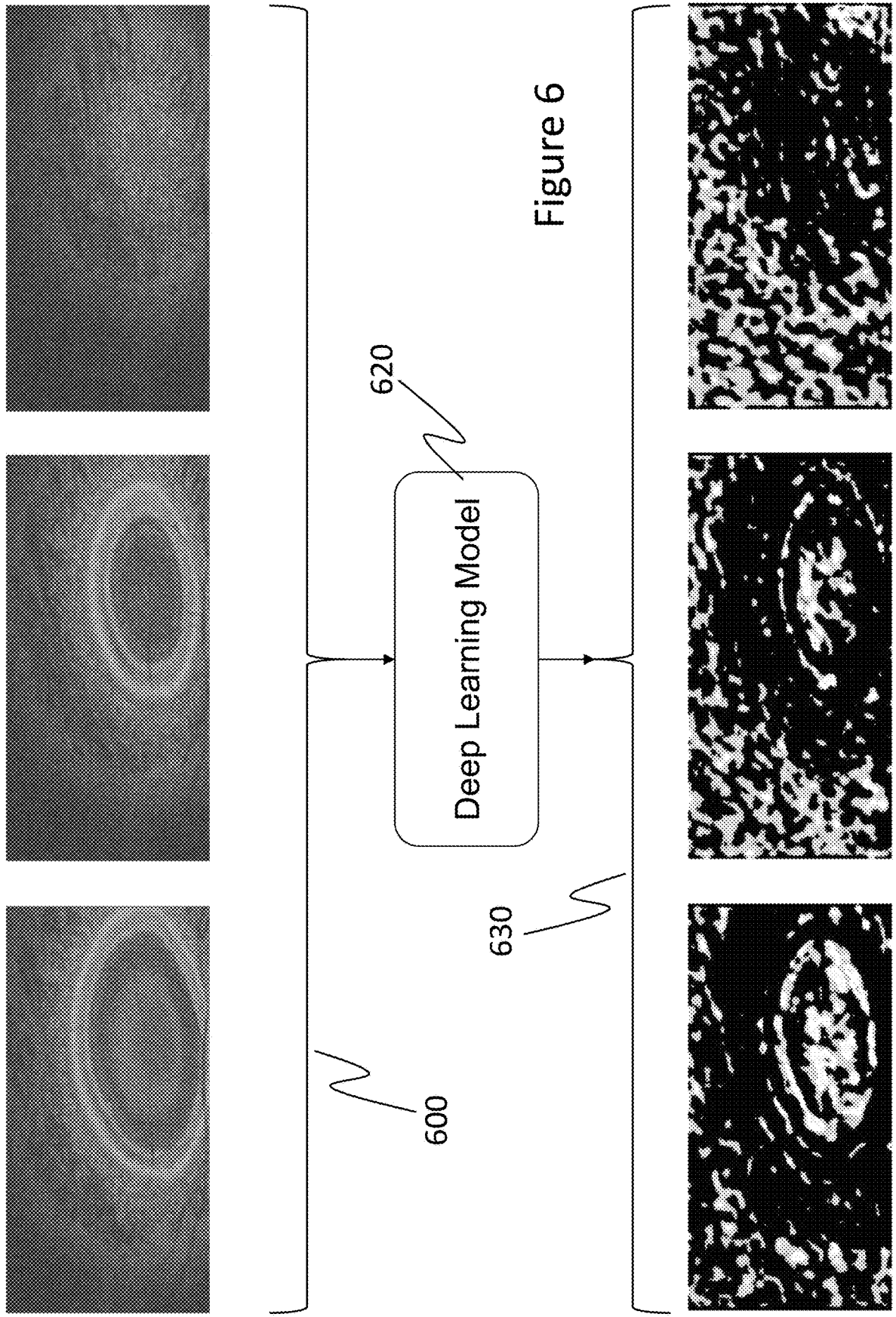
FIG. 6 illustrates a "2D approach" to analyzing input 3D volume data with a learned machine learning system and resulting probability maps.

By way of example, FIG. 6 illustrates such an analysis according to the 2D approach. As shown therein, a plurality of individual en face images 600 from the input 3D volume data are input the trained machine learning system 610. The output of the machine learning system 620 is volumetric probability data, which can be illustrated as a plurality of en face probability maps 630 corresponding to each of the plurality of input en face images 600. Each of the probability maps 630 are indicative of whether any pixels in that image (and thus the corresponding pixels in the input en face images 600) are likely to be within one of the layers that the machine learning system 620 is trained to recognize. During this step, the en face images do not need flattening and can be extracted from the X-Y plane. In the example of FIG. 6, brighter pixels on the probability maps indicate a greater probability that the pixel is from the sclera. Of course, other probability mappings may be used, for example, where darker pixels represent a greater probability; or where probability is indicated by color (e.g., black indicating a low probability and red indicating a high probability, with colors therebetween indicating intermediate probabilities).

Figure 7:
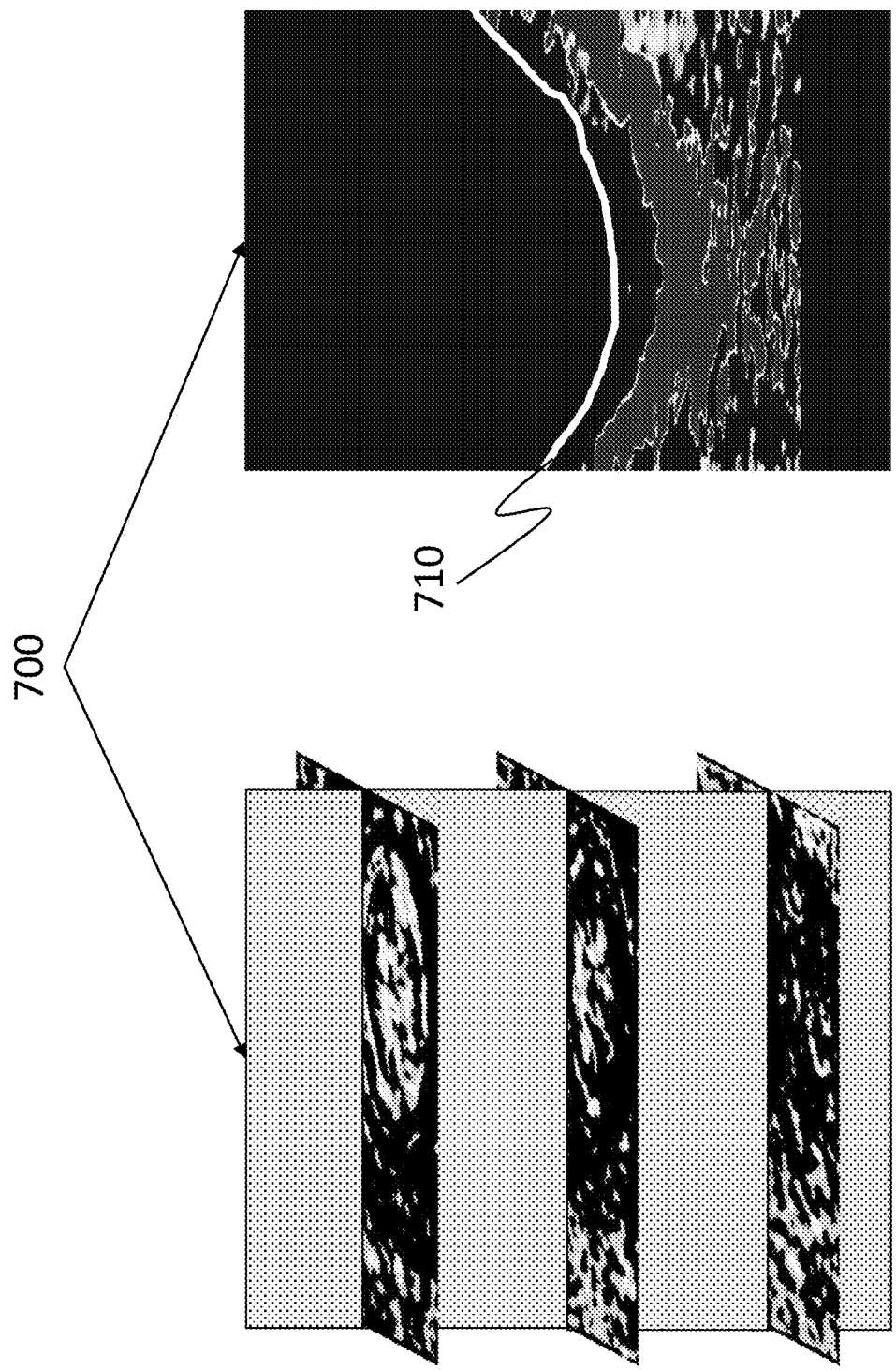
FIG. 7 illustrates an example B-scan probability map generated by a learned machine learning system.

While FIG. 6 illustrates en face probability maps 630 extracted from the volumetric probability data, it is also possible to extract a plurality of B-scans showing the probability data. With reference back to FIG. 1, B-scans are vertical slices extending the z-direction (depth) in an X-Z or Y-Z plane, for example, at through region of interest in the X-Y plane. FIG. 7 illustrates an extracted B-scan probability map 700 from the en face plurality maps 630. In the example of FIG. 7, the resulting B-scan probability map 700 again shows a sclera probability. Further, all probability at depths above the depth corresponding to an identified Bruch's Membrane (BM) 710 (shown by the solid white line) have been set to zero, so only the portion below the BM is analyzed (e.g., to identify the CSI).

Referring again back to FIG. 2, further analysis (e.g., to determine boundaries between, sizes, or other properties of layers) may be performed 240 by applying a thresholding technique to the volumetric data (e.g., in each B-scan of the volume). By way of example, a choroid-sclera interface (CSI) in a B-scan (and in a volume by looking at each B-scan) can be detected by identifying a boundary pixel for each A-line in the B-scan. This detection can be performed directionally (e.g., looking from the outer retina to the inner retina; from top to bottom of the B-scan image), with the boundary pixel being identified, for example, as the first pixel in the A-line with a sclera probability greater than a certain threshold (or the immediately preceding pixel).

Figure 8:
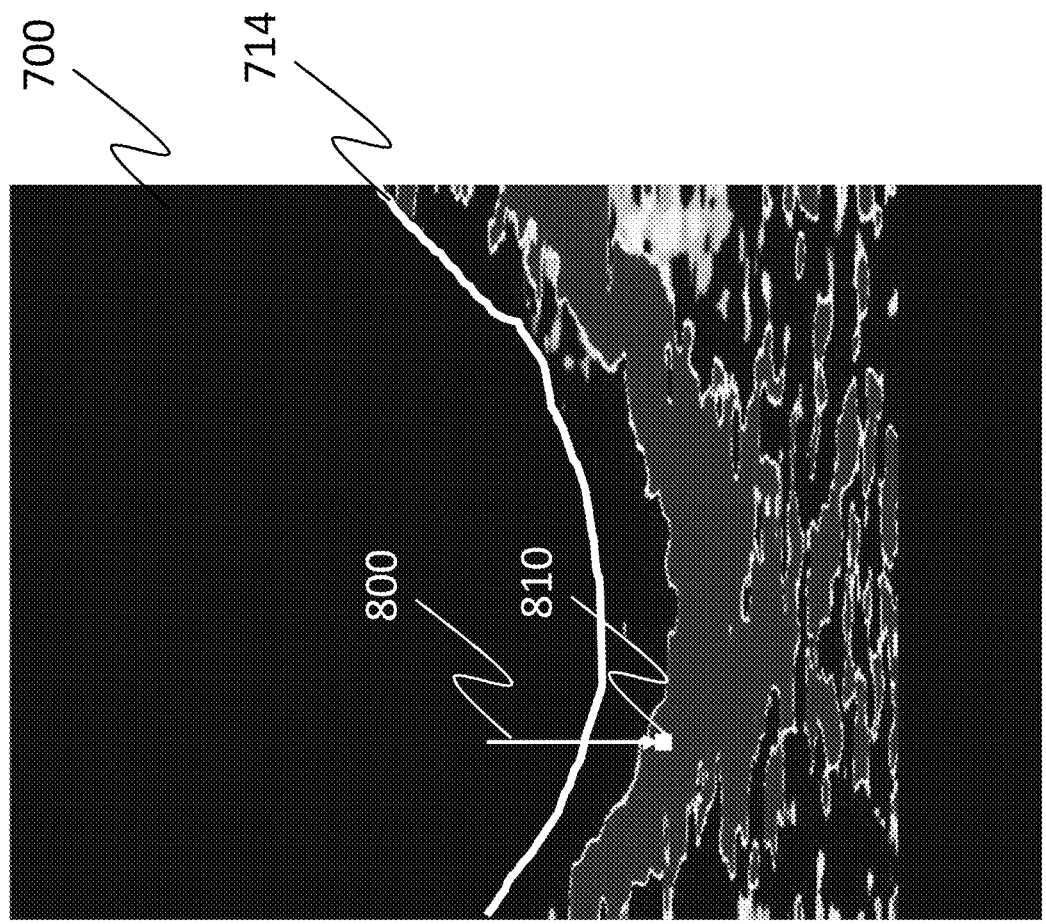
FIG. 8 illustrates an example thresholding analysis of a B-scan probability map.
Figures 9A, 9B, 9C:
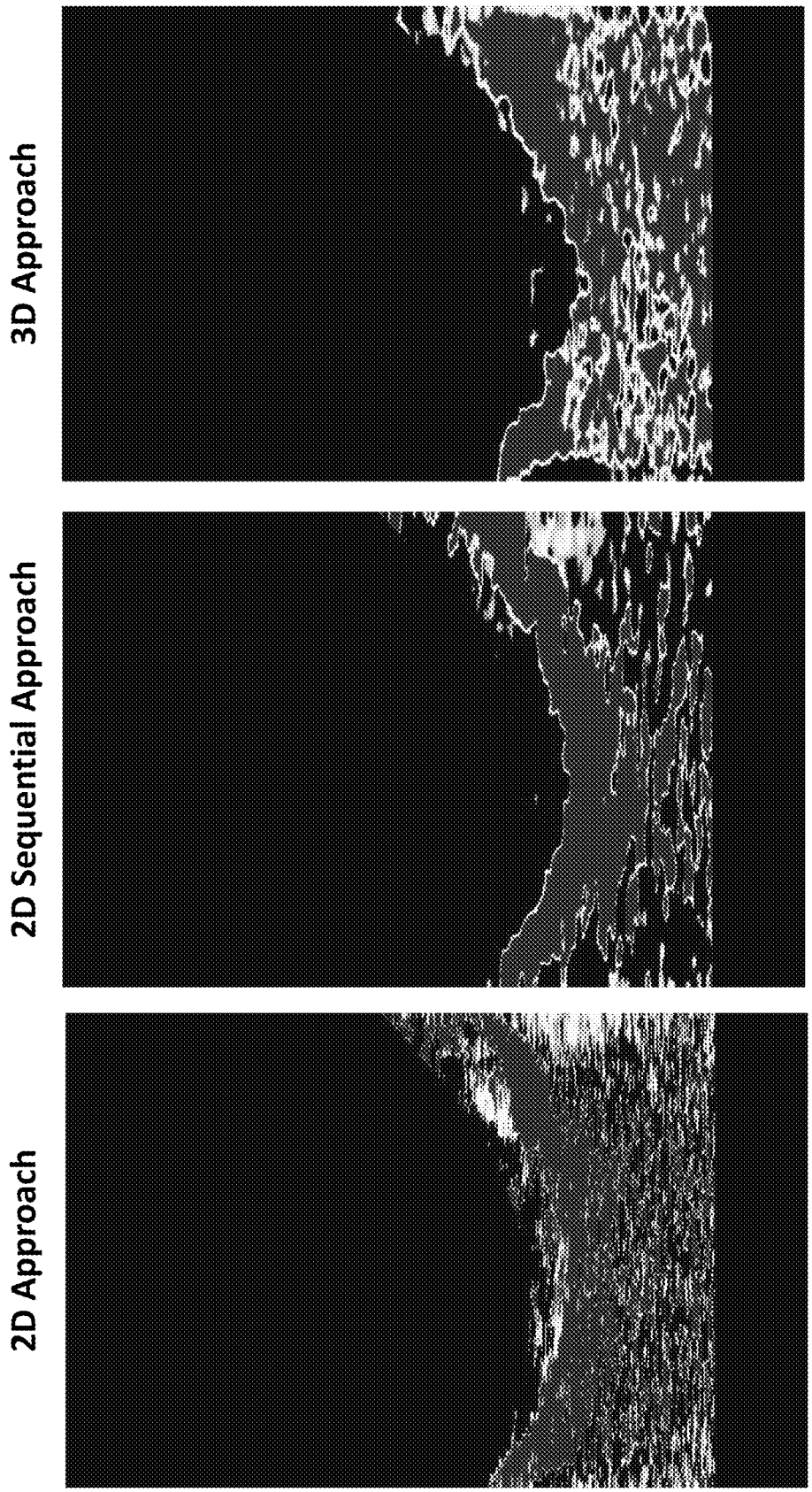
FIG. 9A illustrates a comparative probability map as determined according to the "2D approach" of using a machine learning system.
FIG. 9B illustrates a comparative probability map as determined according to the "2D sequential approach" of using a machine learning system.
FIG. 9C illustrates a comparative probability map as determined according to the "3D approach" of using a machine learning system.
Figure 10B:
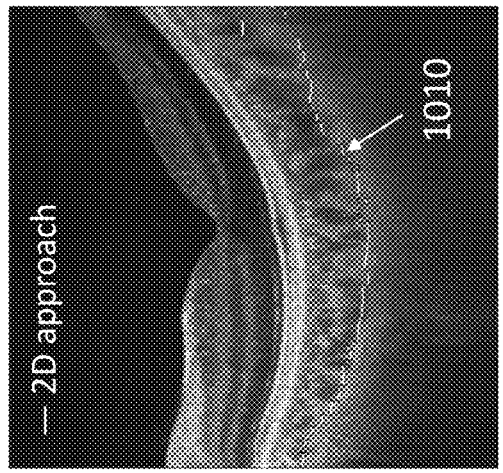
FIG. 10B illustrates a comparative choroid-sclera interface determined from probability data output from a machine learning system according to the "2D approach"
Figure 10D:
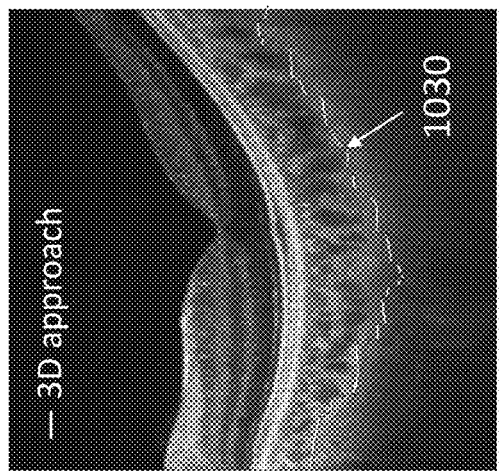
FIG. 10D illustrates a comparative choroid-sclera interface determined from probability data output from a machine learning system according to the "3D approach."
Figure 10A:
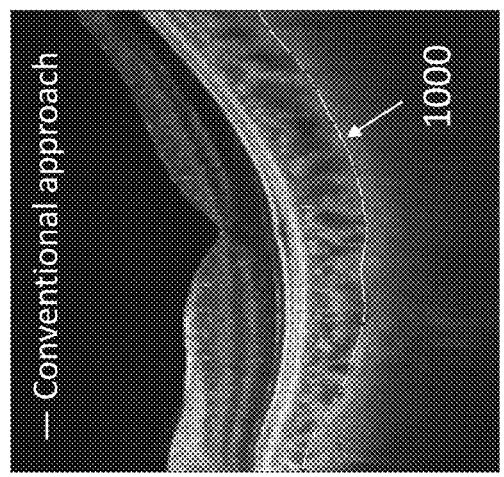
FIG. 10A illustrates a comparative choroid-sclera determined according to conventional techniques.
Figure 10C:
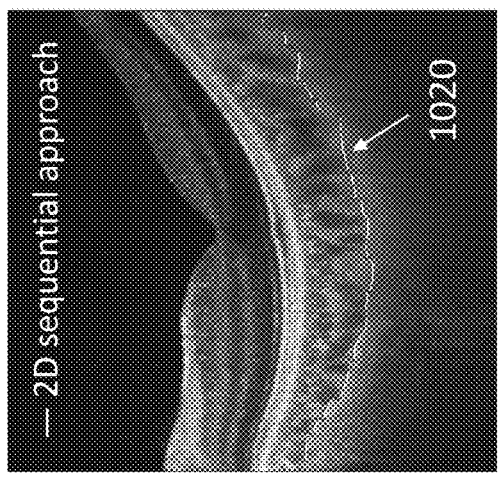
FIG. 10C illustrates a comparative choroid-sclera interface determined from probability data output from a machine learning system according to the "2D sequential approach"

More particularly, with reference to FIG. 8, each A-line in an extracted B-scan 700 may be analyzed from top to bottom (from the outer retina to the inner retina) as shown by arrow 800. Of course, as noted above, analysis may proceed in other directions in some embodiments. During the analysis, a boundary pixel 800 (of the CSI in the example of FIG. 8, as the B-scan probability map shows the probability of pixels being from the sclera) is identified as, for example, 1) the first pixel with a probability equal to or surpassing a predetermined threshold; or 2) the first pixel in a series of pixels that each have a probability equal to or surpassing a predetermined threshold. Regarding the second example, the series of pixels may be any predefined length. For example, if the length is five pixels, the first five consecutive pixels (from top to bottom) having at least the predetermined probability threshold are identified, and the boundary pixel is identified as the first pixel in that series. In this manner, noise or other errors causing a non-boundary pixel to meet the threshold burden can be ignored. In other embodiments, any of the pixels within the series may be identified as the boundary pixel, the first pixel in a layer, or the last pixel in a preceding layer.

In other embodiments, a boundary may be identified using a shortest distance technique, a machine learning (generally, artificial intelligence) technique, or the like. For example, the shortest distance technique can identify the boundary by finding the shortest path from a left most A-line to a right most A-line in a cross-section or other subset of the obtained data, or vice versa. The path length is then determined based on the pixel distance and the probabilities that each pixel belongs to a given layer (e.g., the values from the above-described probability map, where a higher probability yields shorter path). A machine learning technique could identify the boundary by training an algorithm to determine the boundary given the said probability map. During said training procedure, a probability map and the corresponding ground truth boundary is presented to the machine learning system and the system is trained to minimize the difference between a predicted boundary and the ground truth boundary. The machine learning system could be a convolutional neural network, support vector machine, decision tree or of any other architecture. Of course, additional techniques for determining the boundary could also be used.

It is noted that the above methods and approaches are merely exemplary for determining boundaries based on derived probabilities. The present disclosure is not limited to these, and other methods to determine boundaries based on probabilities generated by a machine learning model are envisioned within the scope of the present disclosure. Moreover, additional analysis may be performed beyond identifying boundaries for segmentation to determine other properties of an imaged object. For example, a boundary analysis may be applied to identify upper and lower boundaries of a layer, from which a size/depth of the layer may be identified. Further 3D analysis may be performed over a plurality of 2D images (en face images or B-scans) to determine 3D properties, such as volume. Still further analysis could consider variations in these properties over a 2D area (e.g., a change in depth of a layer over an X-Y region of interest). Additionally analysis may also include post-processing, smoothing of identified boundaries, and the like.

Finally, with reference to FIG. 2, B-scans illustrating the identified boundaries, 3D volumetric images, data associated with further processing, and the like may output or displayed 250, or saved for later use and/or further analysis. Examples of these displays are shown and discussed in more detail, for example, with regard to FIGS. 9-12.

While the above is described with respect to the sclera and choroid, analyzing from top to bottom (from choroid to sclera) to identify the CSI, it is again noted that another direction may also be used. For example, a probability map relating to the probability that each pixel belongs to the choroid can be analyzed from bottom to top (from sclera to choroid) to identify the first pixel in the choroid. This would similarly represent the CSI. These different types of analyses may be performed on any boundary for any structure that the learned machine has been trained to identify the textures of.

FIGS. 9A-C and 10A-D illustrate comparative results for determining probability maps and a resulting choroid-sclera interface identification based on the "2D approach," "2D sequential approach," and "3D approach" of using a machine learning system as described above. As can be seen in FIG. 9, three B-scan probability maps from a same location of interest are illustrated, each map being determined according to a different approach. As noted above, the 2D approach (FIG. 9A) is susceptible to more variation in determining the probability of each pixel because each pixel in an A-line is analyzed individually. Accordingly, the probability map corresponding to the 2D approach exhibits comparatively more noise. The 2D sequential (FIG. 9B) and 3D (FIG. 9C) approaches, on the other hand, are smoother and more closely identify the entire sclera by showing high probabilities for each pixel therein. Similarly, the resulting choroid-sclera interface identification shown in FIGS. 10A-D is comparatively noisier for the 2D approach (1010, FIG. 10B), but remains close to the same interface identified according to a traditional segmentation and smoothing technique (1000, FIG. 10A). The 2D sequential (1020, FIG. 10C) and 3D (1030, FIG. 10D) approaches likewise result in an identified interface similar to the traditional segmentation approach (1000, FIG. 10A), but may be said to provide a more continuous boundary identification.

Figure 11:
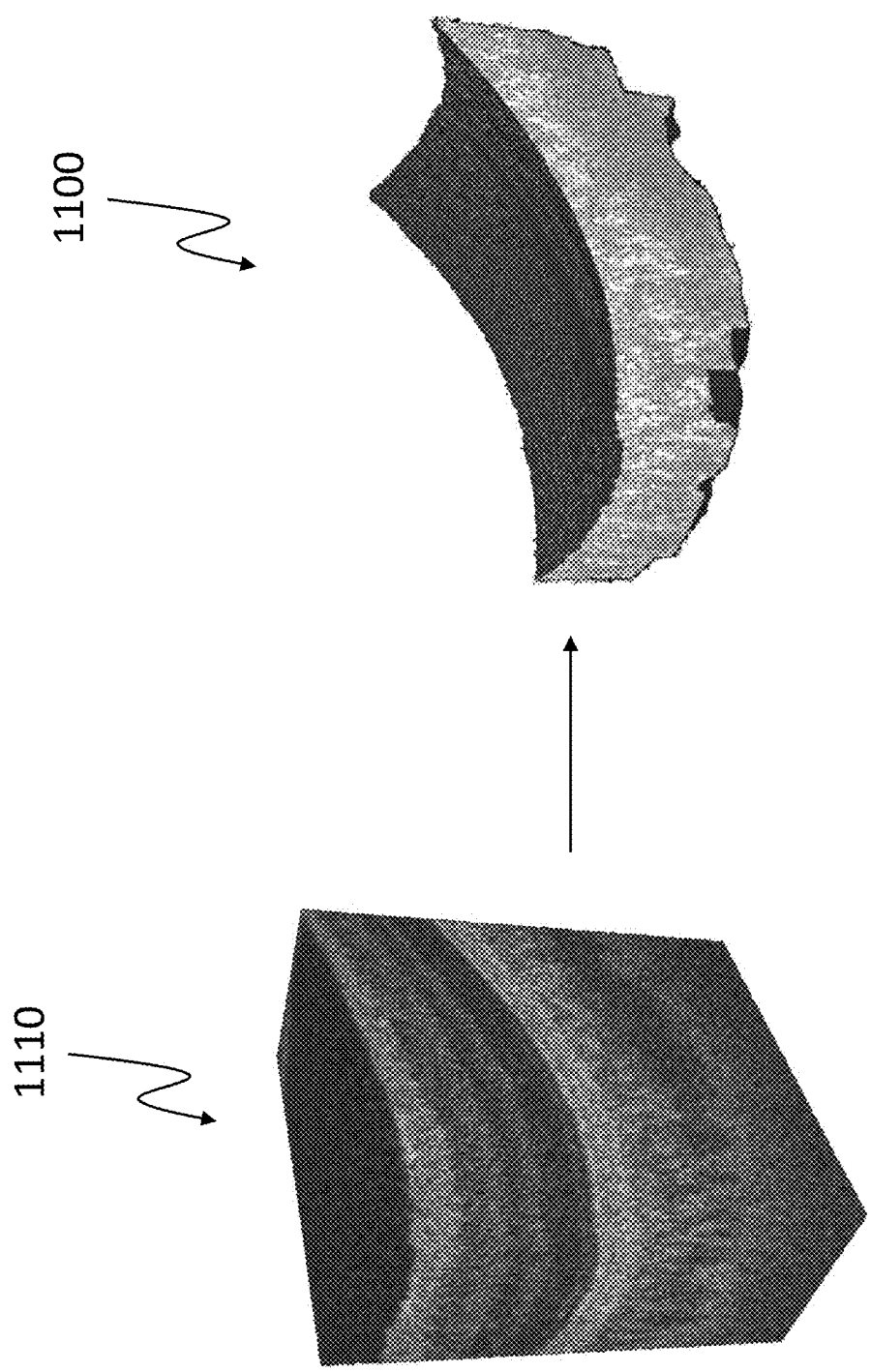
FIG. 11 illustrates an example extracted 3D choroid volumetric image.

FIG. 11 illustrates an example 3D volumetric image of the choroid 1100 extracted from an original volume 1110 that includes each layer of the retina. The original volume 1110 served as data input into a learned machine learning system, from which a choroid probability was output. The choroid 1100 was then extracted by analyzing the choroid probability from the machine learning system. More particularly, by selecting pixels with a layer probability above a predetermine threshold (or any similar method using the said probabilities) throughout the whole 3D volume 1110, a 3D volume of a particular layer (or multiple layers), for example the choroid 1100, may be extracted from the larger 3D volume 1110. In other words, all pixels belonging to a particular layer are identified rather than simply identifying the boundary pixel.

Figure 12:
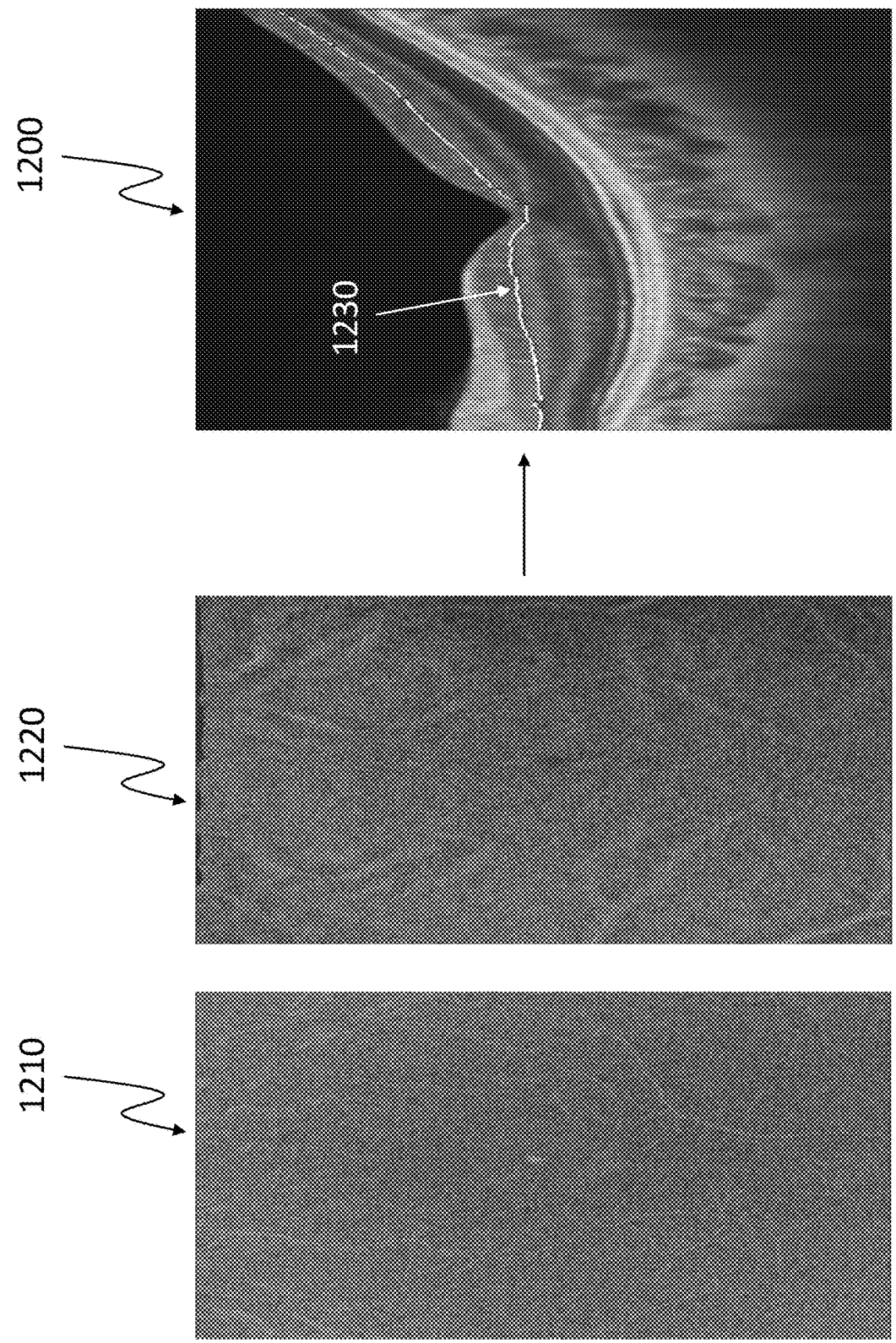
FIG. 12 illustrates identification of the boundary between the ganglion cell layer (GCL) and the inner plexiform layer (IPL) of the retina.

As noted above, while the present disclosure specifically discusses the choroid and sclera, the disclosure is applicable to any layers and boundaries. FIG. 12, for example, illustrates an identification of the boundary between the ganglion cell layer (GCL) and the inner plexiform layer (IPL), according to the description herein. In such an application, the machine learning system is trained to identify the textures of the GCL and IPL, rather than the choroid and sclera as above. An en face image of the GCL 1210 and an en face image of the IPL 1220 are illustrated to show the textural difference in each layer. The resulting determined boundary identification 1230 is shown on B-scan 1200. In still other examples, macular (e.g., retinal ganglion cell layer) regions as well as the optic disk regions (e.g. laminar cribrosa), and/or the cornea, can also be identified and analyzed.

A system configured to perform and execute the methods of the present disclosure is also contemplated. For example, the above methods can be performed on a computer having memory and processor(s) programmed to perform the above-described analysis. The computer may be the same as or different from a computer performing the imaging of a subject (e.g., an OCT machine or slit lamp). The computer may also be a centralized computer accessible by a plurality of remote sites (e.g., clinical sites). The computer may also be the same as or different than the deep learning system.

What is claimed is:

1. A method for analyzing 3D imaging data comprising:
   training a machine learning system with at least two sets of training images, a first set of the training images being obtained from a first type of physiological tissue and a second set of the training images being obtained from a second type of physiological tissue, the machine learning system being trained to recognize differences in the training images between the first and second types of physiological tissues;
   supplying the trained machine learning system with an image of a subject physiological tissue;
   with the trained machine learning system, identifying probabilities that pixels in the image belong to the first type of physiological tissue and/or the second type of physiological tissue, each probability corresponding to a pixel of the image; and
   based on the identified probabilities, identifying a boundary in the image between the first and second types of physiological tissues, or determining a property of the first or second type of physiological tissue, wherein:
   the training images are en face images or multiple en face images forming a volume, and
   the en face images are separated by a predetermined depth.

2. The method of claim 1, wherein the first and second types of physiological tissue are layers of a cornea.

3. The method of claim 1, wherein the en face images are 2D en face images at a single depth or a projection over a depth greater than one pixel.

4. The method of claim 1, wherein the en face images are sequential.

5. The method of claim 1, wherein the first set of training images is from a first 3D volume of training images and the second set of training images is from a second 3D volume of training images, a center of the first 3D volume being a predetermined number of pixels from a center of the second 3D volume.

6. The method of claim 1, further comprising: generating a probability map for the pixels in the image supplied to the trained machine learning system, each pixel of the probability map representing the identified probability of a corresponding pixel of the image supplied to the trained machine learning system.

7. The method of claim 1, further comprising: comparing the identified probabilities for pixels in an A-line of the image supplied to the trained machine learning system to a predetermined threshold.

8. The method of claim 1, wherein the boundary in the image supplied to the machine learning system is identified according to a shortest path search technique.

9. The method of claim 1, wherein the boundary in the image supplied to the machine learning system is identified according to a machine learning technique.

10. The method of claim 1, further comprising: extracting each pixel in the image supplied to the machine learning system that is equal to or greater than a predetermine threshold.

11. The method of claim 1, wherein a plurality of individual en face images of a 3D volume are supplied to the trained machine learning system.

12. The method of claim 1, wherein the differences between the first set and second set of training images are textural differences between the first and second types of physiological tissues.

13. The method of claim 1, further comprising: preprocessing the first set or the second set of training images prior to the machine learning system being trained.

14. The method of claim 1, further comprising: preprocessing the image of the subject physiological tissue prior to supplying the trained machine learning system with the image.

15. The method of claim 1, wherein at least one of the training images or the image of the subject physiological is obtained by a slit lamp.

16. The method of claim 3, wherein the 2D en face images are generated by flattening a 3D volume with respect to a reference layer.

17. The method of claim 7, wherein a boundary pixel in the A-line is identified as the first pixel whose probability is equal to or greater than the predetermined threshold, the boundary pixel being a pixel of the identified boundary.

18. The method of claim 7, wherein a boundary pixel in the A-line is identified as the first pixel in a set of pixels, each pixel in the set of pixels having an identified probability that is equal to or greater than the predetermined threshold.

19. The method of claim 10, wherein the extracted pixels form a 3D volume and the method further comprises displaying the 3D volume formed by the extracted pixels.

* * * * *